US008653051B2

(12) United States Patent
Tuiten et al.

(10) Patent No.: US 8,653,051 B2
(45) Date of Patent: Feb. 18, 2014

(54) USE OF 3-ALPHA-ANDROSTANEDIOL IN COMBINATION WITH A PDE5 INHIBITOR, IN THE TREATMENT OF SEXUAL DYSFUNCTION

(75) Inventors: Jan Johan Adriaan Tuiten, Almere (NL); Johannes Martinus Maria Bloemers, Almere (NL); Robertus Petrus Johannes De Lange, Hilversum (NL)

(73) Assignee: Emotional Brain B.V., Almere (NL)

( * ) Notice: Subject to any disclaimer, the term of this patent is extended or adjusted under 35 U.S.C. 154(b) by 932 days.

(21) Appl. No.: 12/513,355

(22) PCT Filed: Nov. 2, 2007

(86) PCT No.: PCT/NL2007/050534
§ 371 (c)(1),
(2), (4) Date: Mar. 1, 2010

(87) PCT Pub. No.: WO2008/054214
PCT Pub. Date: May 8, 2008

(65) Prior Publication Data
US 2010/0152145 A1      Jun. 17, 2010

(30) Foreign Application Priority Data

Nov. 3, 2006   (EP) .................................... 06076976

(51) Int. Cl.
*A61K 31/56* (2006.01)
(52) U.S. Cl.
USPC .......................................... 514/170; 514/171
(58) Field of Classification Search
USPC ................................................ 514/170, 171
See application file for complete search history.

(56) References Cited

U.S. PATENT DOCUMENTS

| | | |
|---|---|---|
| 3,976,776 A | 8/1976 | Wu et al. |
| 4,521,421 A | 6/1985 | Foreman |
| 4,596,795 A | 6/1986 | Pitha |
| 4,640,921 A | 2/1987 | Othmer et al. |
| 4,833,142 A | 5/1989 | Hartog et al. |
| 4,877,774 A | 10/1989 | Pitha et al. |
| 5,015,646 A | 5/1991 | Simms |
| 5,250,534 A | 10/1993 | Bell et al. |
| 5,389,687 A | 2/1995 | Schaus et al. |
| 5,565,466 A | 10/1996 | Gioco et al. |
| 5,731,339 A | 3/1998 | Lowrey |
| 5,877,216 A | 3/1999 | Place et al. |
| 6,165,975 A | 12/2000 | Adams et al. |
| 6,242,436 B1 | 6/2001 | Llewellyn |
| 6,246,436 B1* | 6/2001 | Lin et al. ........................ 348/308 |
| 6,251,436 B1 | 6/2001 | Drizen et al. |
| 6,294,550 B1 | 9/2001 | Place et al. |
| 6,306,841 B1 | 10/2001 | Place et al. |
| 6,423,683 B1 | 7/2002 | Heaton et al. |
| 6,428,769 B1 | 8/2002 | Rubsamen et al. |
| 6,469,012 B1 | 10/2002 | Ellis et al. |
| 6,469,016 B1 | 10/2002 | Place et al. |
| 6,472,434 B1 | 10/2002 | Place et al. |
| 6,541,536 B2 | 4/2003 | Weikard et al. |
| 6,608,065 B1 | 8/2003 | Daugan |
| 6,610,652 B2 | 8/2003 | Adams et al. |
| 6,632,419 B2 | 10/2003 | Rubsamen et al. |
| 6,964,780 B1 | 11/2005 | King et al. |
| 7,151,103 B2 | 12/2006 | Borsini et al. |
| 7,198,801 B2 | 4/2007 | Carrara et al. |
| 2003/0022877 A1 | 1/2003 | Dudley |
| 2003/0027804 A1 | 2/2003 | Van der Hoop |
| 2003/0104980 A1 | 6/2003 | Borsini et al. |
| 2004/0014761 A1 | 1/2004 | Place et al. |
| 2004/0186086 A1* | 9/2004 | Bunschoten et al. ......... 514/182 |
| 2004/0208829 A1 | 10/2004 | Rubsamen et al. |
| 2005/0152956 A1 | 7/2005 | Dudley |
| 2006/0040935 A1 | 2/2006 | Maytom et al. |
| 2006/0270642 A1 | 11/2006 | Lehman et al. |
| 2006/0281752 A1 | 12/2006 | Heaton et al. |
| 2006/0287335 A1 | 12/2006 | Sukoff Rizzo et al. |
| 2007/0093450 A1 | 4/2007 | Tuiten |
| 2007/0149454 A1 | 6/2007 | Mattern |
| 2007/0154533 A1 | 7/2007 | Dudley |
| 2009/0306026 A1 | 12/2009 | Tuiten et al. |
| 2010/0093680 A1 | 4/2010 | Tuiten et al. |
| 2010/0152145 A1 | 6/2010 | Tuiten et al. |
| 2010/0160270 A1 | 6/2010 | Tuiten et al. |

FOREIGN PATENT DOCUMENTS

| | | |
|---|---|---|
| EP | 2000143 | 12/2008 |
| JP | 11-504902 | 5/1999 |
| JP | 2003-530430 | 10/2003 |
| JP | 2004-520320 | 7/2004 |
| NZ | 524601 | 4/2006 |
| RU | 2130776 | 5/1999 |
| RU | 97117167 | 10/1999 |
| RU | 2152787 | 7/2000 |
| RU | 2180591 | 3/2002 |

(Continued)

OTHER PUBLICATIONS

International Preliminary Report on Patentability for PCT/NL2007/050534, mailed on Jul. 2, 2009, 8 pages.

(Continued)

*Primary Examiner* — San-Ming Hui
(74) *Attorney, Agent, or Firm* — Morrison & Foerster LLP

(57) ABSTRACT

The invention relates to the field of male and/or female sexual dysfunction. The invention specifically relates to the use of 3-alpha-androstanediol, preferably in combination with a type 5 phosphodiesterase (PDE5) inhibitor.

5 Claims, No Drawings

(56) References Cited

FOREIGN PATENT DOCUMENTS

| | | |
|---|---|---|
| RU | 2285519 | 10/2006 |
| WO | WO-94/28902 | 12/1994 |
| WO | WO-95/05188 | 2/1995 |
| WO | WO-95/33486 | 12/1995 |
| WO | WO-96/28142 | 9/1996 |
| WO | WO-96/33705 | 10/1996 |
| WO | WO-96/36339 | 11/1996 |
| WO | WO-97/03675 | 2/1997 |
| WO | WO-99/21562 | 5/1999 |
| WO | WO-99/62502 | 9/1999 |
| WO | WO-00/66084 | 11/2000 |
| WO | WO-01/78703 | 10/2001 |
| WO | WO-02/26214 | 4/2002 |
| WO | WO-02/051420 | 7/2002 |
| WO | WO-02/069906 | 9/2002 |
| WO | WO-03/002123 | 1/2003 |
| WO | WO-03/011300 | 2/2003 |
| WO | WO-2004/037173 | 5/2004 |
| WO | WO-2004/037262 | 5/2004 |
| WO | WO-2005/007166 | 1/2005 |
| WO | WO-2005/039530 | 5/2005 |
| WO | WO-2005/094827 | 10/2005 |
| WO | WO-2005/102342 | 11/2005 |
| WO | WO-2005/107810 | 11/2005 |
| WO | WO-2006/127057 | 11/2006 |
| WO | WO-2007/054791 | 5/2007 |
| WO | WO-2007/055563 | 5/2007 |

OTHER PUBLICATIONS

Fourcroy, Drugs (2003) 63:1445-1457.
Berman et al., Journal of Urology (2003) 170(6):2333-2338.
Kuhn, Rec. Progress Hormone Research (2002) Academic Press vol. 57, pp. 411-434.
Shifren et al., New England Journal of Medicine (2000) 343:682-688.
Spungen et al., The Mount Sinai Journal of Medicine (1999) 66:201-205.
Traish et al., Drug Discovery Today: Disease Mechanisms (2004) 1(1):91-97.
International Search Report for PCT/NL2007/050534, mailed on Feb. 24, 2009, 3 pages.
Morali et al., Biology of Reproduction (1994) 51(3):562-571.
Belikov et al., Pharmaceutical Chemistry (1993) 43-47 (machine translation provided).
Doggrell, "Comparison of Clinical Trials with Sildenafil, Vardenafil and Tadalafil in Erectile Dysfunction," Expert Opin. Pharmacother. (2005) 6(1):1-2. (abstract).
Dyson et al., May's Chemistry of Synthetic Drugs, ($5^{th}$ ed. 1959) (machine translation provided).
Frye et al., "Behavioral Effects of 3 Alpha-Androstanediol.1: Modulation of Sexual Receptivity and Promotion of GABA-Stimulated Chloride Flux," Behav. Brain Res. (1996) 79 (1-2):109-118. (abstract).
Graham-Smith et al., Oxford Handbook of Clinical Pharmacology and Pharmacotherapy (2000) 18-20 (machine translation provided).
Haensel et al., "Flesinoxan: A Prosexual Drug for Male Rats," European Journal of Pharmacology (1997) 330:1-9.
Kharkevich et al., Pharmacology ($3^{rd}$ ed. 1987) 41-42 (machine translation provided).
Koolman et al., Biochemistry (1998) 365 (machine translation provided).
Phillips, "Female Sexual Dysfunction: Evaluation and Treatment," Am Fam Physician (2000) 62(1): 127-136, 141-142.
Rendell et al., "Sildenafil for Treatment of Erectile Dysfunction in Men with Diabetes A Randomized Controlled Trial," JAMA (1999) 281(5):421-426.
Sher et al., "Vaginal Sildenafil (Viagra): A Preliminary Report of a Novel Method to Improve Uterine Artery Blood Flow and Endometrial Development in Patients Undergoing IVF," Human Reproduction (2000) 15(4):805-809.
Shields et al., "Use of Sildenafil for Female Sexual Dysfunction," Ann. Pharmacother. (2006) 40:931-934.
The Merck Manual of Diagnosis and Therapy 30-36 (Robert Berkow, M.D. et al. eds., Merck Research Laboratories, Merck & Co., Inc. 1992) (1997) (machine translation provided).
The RLS Encyclopedia of Drugs, RLS 2004, vol. 11 (machine translation provided).
Tuiten et al., "Time Course of Effects of Testosterone Administration on Sexual Arousal in Women," Arch. Gen. Psychiatry (2000) 57:149-153.
Vidal's Handbook, Drugs in Russia, Moscow AstraPharmService 2001 (machine translation provided).
Rasio-Filho et al. (1996) "Effects of 8-OH_DPAT on Sexual Behavior of Male Rats Castrated at Different Ages," Hormones and Behavior 30:251-258.
Singh et al. (2006) "Pharmokinetics of a Testosterone Gel in Healthy Postmenopausal Women," The Journal of Clinical Endocrinology & Metabolism 91(1):136-144.
International Preliminary Report on Patentability for International Patent Application No. PCT/NL2007/050533, mailed Jul. 2, 2009, 8 pages.
International Search Report for International Patent Application No. PCT/NL2007/050533, mailed Feb. 25, 2009, 3 pages.
International Preliminary Report on Patentability for International Patent Application No. PCT/NO2007/050535, mailed Jul. 2, 2009, 9 pages.
International Search Report for International Patent Application No. PCT/NO2007/050535, mailed Feb. 24, 2009, 3 pages.
International Search Report for International Patent Application No. PCT/NL2005/000355, mailed Dec. 18 2006, 5 pages.
International Search Report for International Patent Application No. PCT/NL2006/000542, mailed Jul. 17, 2007, 5 pages.
Written Opinion of the International Searching Authority for PCT/NL2007/050533, issued May 5, 2009, 5 pages.

* cited by examiner

USE OF 3-ALPHA-ANDROSTANEDIOL IN COMBINATION WITH A PDE5 INHIBITOR, IN THE TREATMENT OF SEXUAL DYSFUNCTION

CROSS-REFERENCE TO RELATED APPLICATIONS

This application is the national phase of PCT application PCT/NL2007/050534 having an international filing date of 2 Nov. 2007, which claims benefit of European patent application No. 06076976.7 filed 3 Nov. 2006. The contents of the above patent applications are incorporated by reference herein in their entirety.

The invention relates to the field of male and/or female sexual dysfunction. The invention specifically relates to the on demand use of 3-alpha-androstanediol, preferably in combination with a type 5 phosphodiesterase (PDE5) inhibitor.

Male Sexual Dysfunction (MSD) refers to various disturbances or impairments of male sexual function, including inhibited sexual desire (ISD), erectile dysfunction (ED) or impotence and premature ejaculation (PE, also known as rapid ejaculation, early ejaculation, or ejaculation praecox) and anorgasmia. ED is treated successfully using PDE5 inhibitors such as sildenafil, vardenafil and tadalafil. Current successful treatment for PE includes anaesthetic creams (like lidocaine, prilocaine and combinations) that reduce sensation on the penis and SSRI antidepressants such as paroxetine, fluoxetine and sertraline. There is currently no known successful medication for ISD.

Female Sexual Dysfunction (FSD) refers to various disturbances or impairments of sexual function, including a lack of interest in sexual activity, repeated failure to attain or maintain sexual excitement, inability to attain an orgasm following sufficient arousal. A recent study estimated that 43% of women suffer from sexual dysfunction in the USA[1]. Low sexual desire (22% prevalence) and sexual arousal problems (14% prevalence) belong to the most common categories of sexual dysfunction of women. These categories are convenient in providing working definitions and an accepted lexicon for researchers and therapists. However, it may be incorrect to assume that these disorders are fully independent of each other. Both case studies and epidemiological studies demonstrate that these disorders can overlap and may be interdependent. In some cases, it may be possible to identify the primary disorder that led to the others, but in many cases, this may be impossible.

3-alpha-androstanediol is described in U.S. Pat. No. 6,242,436 B1 as an alternative to androgen repletion therapy and for androgen decrease/depletion related problems in humans. The described purpose of this substitution lies in the replenishment of subphysiological serum concentrations of dihydrotestosterone (DHT) via 3-alpha-androstanediol administration. Also, the mechanism of effect of decreasing androgen decrease/depletion related problems lies in the replenishment of (DHT), according to U.S. Pat. No. 6,242,436 B1. Androgen depletion can decrease sexual motivation. However, decreased sexual motivation is often not caused by abnormal androgen concentrations.

For the treatment of male and/or female sexual disorder a number of different treatments, with greater or lesser degrees of success have been suggested and applied. For example, WO 2005/107810 describes the use of testosterone and a type 5 phosphodiesterase (PDE5) inhibitor which components must be released within a certain order and timeframe in respect of sexual activity. Although this treatment provides promising results, the used timeframes are considered to be undesirably long within the context of anticipation of sexual activity. Moreover, the treatment described in WO 2005/107810 is somewhat complicated because, depending on the formulation of the active ingredients, the active ingredients have to be administered within a certain order and/or timeframe. In persons who are not very accurate in taking the right active ingredients at the right time points, the goal of treating sexual dysfunction may not or only partially be reached.

The present invention discloses that 3-alpha-androstanediol administration induces increased sexual motivation and increased attention for sexual cues in men with MSD and women with FSD. These 3-alpha-androstanediol administration dependant increases in motivation and attention are independent of prior physiological androgen concentrations; 3-alpha-androstanediol administration will increase sexual motivation and attention for sexual cues in men and women with normal (i.e. physiological) or with subphysiological androgen levels alike.

The present invention discloses further that the time frame between the intake of the active ingredients and sexual activity can be decreased by using 3-alpha-androstanediol (compared to sublingual testosterone) and a PDE5-inhibitor. Moreover, in one of the embodiments the active ingredients can be administered at the same time point, hence minimising the risk of forgetting to take one of the ingredients at all or in time. The obtained results are comparable to the ones obtained with the compounds described in WO 2005/107810. This is considered to be a surprise, because 3-alpha-androstanediol is a much weaker androgen when compared to testosterone and also because 3-alpha-androstanediol is suggested to have an effect on a different receptor, the GABAA receptor [2] (again when compared to testosterone). Another advantage of 3-alpha-androstanediol over testosterone are lower side effects on masculinisation and lower risk for cancer since testosterone is not given and can thus not be reduced to estradiol.

In a first embodiment, the invention provides the use of 3-alpha-androstanediol in the preparation of a medicament for the treatment of sexual dysfunction. The term sexual dysfunction refers to male and/or female sexual dysfunction.

3-alpha-androstanediol is also known as 5α-androstane 3α, 17β-diol and is one of testosterone's metabolites. Testosterone, can be converted to 5α-dihydrotestosterone (DHT) by 5α-reductases. DHT is then further converted to 3-alpha-androstanediol by 3α-hydroxysteroid dehydrogenase (also known as 3-oxidoreductase and 3α-hydroxysteroid-oxidoreductase, 3α-HSD reductase hereafter). The conversion from testosterone to DHT is unidirectional; the conversion of DHT to 3-alpha-androstanediol is bi-directional: 3α-HSD oxidases can also convert 3-alpha-androstanediol to DHT. The 3α-HSD reductase/oxidase equilibrium appears to be auto regulated by circulating steroid hormones such as testosterone, DHT and 3-alpha-androstanediol, but also oestrogen, growth hormone and the stress related glucocorticoids [3]. Three human isoforms of 3α-HSD reductase exist, two of which are also found in the brain (h3α-HSD2 and 3, also known as AKR 1C2 and AKR 1C3).

According to the invention the level of free 3-alpha-androstanediol should preferably be a peak plasma level of at least of 10-100 times and preferably of 5-100 times the normal serum levels [4] (i.e. 0.6-6 and preferably 0.3-6 ng/l for women and 2.2-22 and preferably 1.1-22 ng/l for men), which will typically occur between 1 and 60 minutes after administration of the 3-alpha-androstanediol.

3-alpha-androstanediol is preferably given in a formulation wherein there is a sharp and rapid increase of 3-alpha-androstanediol in the blood circulation of the subject to whom it is administered. The invention therefore provides a use, wherein the 3-alpha-androstanediol is provided in the form of a sublingual formulation, such as a sublingual formulation comprising cyclodextrins as carrier. Another example of a suitable route of administration is buco-mucosally or intranasally, which can also be performed with the use of a cyclodextrin formulation or other usual excipients, diluents and the like. A typical example of a formulation is given in hydroxypropyl-beta cyclodextrin, but other beta cyclodextrins and other usual excipients, diluents and the like are within the skill of the art for preparing a formulation comprising 3-alpha-androstanediol, which releases essentially all of the 3-alpha-androstanediol within one short burst. Said burst will typically be within a short time interval (for example within 60-120 seconds, more preferably within 60 seconds) upon administration, leading to blood peak levels of 3-alpha-androstanediol about 1-60 minutes later, lasting for at least 180 minutes from time of application.

3-alpha-androstanediol in the circulation is bound by SHBG (steroid hormone binding globulin) and by albumin. It is important that the peak plasma level of 3-alpha-androstanediol as defined in the present invention is present and calculated as free 3-alpha-androstanediol, so a fraction not bound by albumin and SHBG. Thus the dose of 3-alpha-androstanediol given should be high enough to saturate the albumin and SHBG (i.e. the concentration of 3-alpha-androstanediol must be high enough to overcome complete binding of 3-alpha-androstanediol by SHBG or albumin), or another way of avoiding binding to albumin or SHBG must be designed, such as the use of a competitor for the 3-alpha-androstanediol binding site on SHBG.

In contrast to other sexual dysfunction treatments based on 3-alpha-androstanediol, the use (and method) described herein aim at a temporary increase in the 3-alpha-androstanediol level in the treated subject. Other methods aim at restoring/replacing/replenishing the 3-alpha-androstanediol levels (or that of its metabolites such as DHT) to normal (i.e. physiological) levels as found in a normal subject. In a preferred embodiment, 3-alpha-androstanediol is applied such that a short-lasting (several hours) supraphysiological peak of 3-alpha-androstanediol in the blood circulation of the subject to whom it is administered, is obtained. Thereafter, the level returns to baseline (i.e. the level before administration).

In a second embodiment, the invention provides the use of 3-alpha-androstanediol and a type 5 phosphodiesterase (PDE5) inhibitor in the preparation of a medicament for the treatment of sexual dysfunction. The term sexual dysfunction refers to male and/or female sexual dysfunction.

As described above one of the problems associated with current treatment is the large time delay between the intake of active ingredients and sexual activity. With the 3-alpha-androstanediol embodiments of the present invention the time delay is shortened from approximately 4 hours to approximately 1 hour. This results in a decrease of approximately 3 hours.

Multiple PDE5 inhibitors are available. An example of a PDE5 inhibitor is vardenafil HCl which is designated chemically as piperazine, 1-[[3-(1,4-dihydro-5-methyl-4-oxo-7-propylimidazo[5,1-f][1,2,4]triazin-2-yl)-4-ethoxyphenyl]sulfonyl]-4-ethyl-, monohydrochloride. In addition to the active ingredient, vardenafil HCl, each tablet contains microcrystalline cellulose, crospovidone, colloidal silicon dioxide, magnesium stearate, hypromellose, polyethylene glycol, titanium dioxide, yellow ferric oxide, and red ferric oxide. Another example is given in sildenafil citrate which is chemically designated as 1-[[3-(6,7-dihydro-1-methyl-7-oxo-3-propyl-1Hpyrazolo[4,3-d]pyrimidin-5-yl)-4-ethoxyphenyl] sulfonyl]-4-methylpiperazine citrate. In addition to the active ingredient, sildenafil citrate, each tablet contains the following ingredients: microcrystalline cellulose, anhydrous dibasic calcium phosphate, croscarmellose sodium, magnesium stearate, hydroxypropyl methylcellulose, titanium dioxide, lactose, triacetin, and FD & C Blue #2 aluminum lake. Another example is given in tadalafil which is chemically designated as pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-. In addition to the active ingredient, tadalafil, each tablet contains the following ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide, and triacetin.

The number of PDE5-inhibitors is still expanding and other non-limiting examples are: E-4021, E-8010, E-4010, AWD-12-217 (zaprinast), AWD 12-210, UK-343,664, UK-369003, UK-357903, BMS-341400, BMS-223131, FR226807, FR-229934, EMR-6203, Sch-51866, IC485, TA-1790, DA-8159, NCX-911 or KS-505a or the compounds disclosed in WO 96/26940.

It is clear to the skilled person that the active ingredients are preferably administrated/released such that their peak effects (i.e. their activities) at least partly overlap/coincide and preferably completely overlap. In respect of testosterone and 3-alpha-androstanediol the peak effect means the maximal increase in attention to erotic stimuli and in sexual motivation. For a PDE5 inhibitor the peak effect is the maximal increase in activity of the NANC (non adrenergic non cholinergic) pathway of the autonomous nervous system. This goal can be reached by using different strategies. One non-limiting example is provided.

In a preferred embodiment, said 3-alpha-androstanediol and said PDE5 inhibitor are essentially released at the same time. The term "at essentially the same time" should be understood to mean that preferably 3-alpha-androstanediol and a PDE5 inhibitor reach their peak serum levels within the to be treated subject within 30 minutes from each other, preferably 25-30 minutes, more preferably 20-25 minutes, even more preferably 15-20 or 10-15 minutes and most preferably the two compounds are released in the subject within 0 to 10 minutes from each other.

As outlined above, for an optimal effect of 3-alpha-androstanediol and a PDE5 inhibitor, it is desired that the peak effect of both compounds coincide. However, even if the peak effects only overlap partly, this still results in the desired effect (for example, treatment of FSD). There is a time lag for the effect of 3-alpha-androstanediol of about 1-60 minutes (and oral administration of 3-alpha-androstanediol could lengthen this even further) and the effect of 3-alpha-androstanediol lasts for approximately 3 hours. PDE5-inhibitors such as vardenafil and sildenafil typically reach their peak plasma concentration (which should be at least 35 ng/ml for sildenafil, 2 µg/l for vardenafil and 40 µgl for tadalafil) after about 1 hour after administration and their effect is then also present. By releasing 3-alpha-androstanediol and a PDE5 inhibitor at essentially the same time, their effects at least partly coincide. It is clear to the skilled person that 3-alpha-androstanediol and a PDE5 inhibitor can be formulated such that their release is delayed. For example, the active ingredients are provided with or surrounded by a coating, which is dissolved after 2 hours. In such a case, the active ingredients must be taken 2-3 hours before sexual activity. Other variations are easily performed by the skilled person and are within the scope of the present invention.

Reference herein to sexual dysfunction includes male and/or female sexual dysfunction. Reference to male sexual dysfunction includes inhibited sexual desire (ISD), erectile dysfunction (ED) and premature ejaculation (PE). Reference to female sexual dysfunction includes Hypoactive Sexual Desire Disorder (HSDD), Female Sexual Arousal Disorder (FSAD) and Female Orgasmic Disorder (FOD).

For the present invention the routes of administration of choice are those which are the least invasive (for example oral, buco-mucosal or intranasal). Motivation for sexual behaviour should not be negatively influenced by invasive routes of administration.

The use as described herein may alternatively be formulated as: 3-alpha-androstanediol and a PDE5-inhibitor for use in a method for treating sexual dysfunction.

In a preferred embodiment, the invention provides use of 3-alpha-androstanediol and a type 5 phosphodiesterase (PDE5) inhibitor in the preparation of a medicament for the treatment of female sexual dysfunction. In yet another preferred embodiment, said female sexual dysfunction is female sexual arousal disorder (FSAD) and/or hypoactive sexual desire disorder (HSDD) and/or female orgasmic disorder (FOD).

In yet another preferred embodiment, said sexual dysfunction is male sexual dysfunction.

The invention also provides a pharmaceutical composition comprising 3-alpha-androstanediol.

3-alpha-androstanediol is preferably provided in the form of a sublingual formulation, for example a sublingual formulation comprising cyclodextrins as carrier. Another example of a suitable route of administration is buco-mucosally or intranasally, which can also be performed with the use of a cyclodextrin formulation or other usual excipients, diluents and the like. In a preferred embodiment, the pharmaceutical is designed for sublingual administration and even more preferred said composition comprises cyclodextrin such as hydroxypropyl-beta cyclodextrin. A typical non/limiting example of a prepared 3-alpha-androstanediol sample (for 0.1-0.5 mg of 3-alpha-androstanediol) consists of 0.1-0.5 mg 3-alpha-androstanediol, 5 mg hydroxypropyl-betacyclodextrines (carrier), 5 mg ethanol, and 5 ml water, but each of the amounts of these substances might be higher or lower.

In yet another embodiment, the invention provides a pharmaceutical composition comprising 3-alpha-androstanediol and a PDE5 inhibitor. The pharmaceutical composition comprising a PDE5-inhibitor preferably comprises at least 25 mg sildenafil (or 5 mg vardenafil, or 5 mg tadalafil) and at most 100 mg sildenafil (or 20 mg vardenafil, or 20 mg tadalafil), or comparable dosages of other PDE5-inhibitors. These doses may vary with the weight of the patient and are preferably determined by a physician.

In a preferred embodiment, the invention provides a pharmaceutical composition comprising 3-alpha-androstanediol and a PDE5 inhibitor, wherein said composition is designed to release said 3-alpha-androstanediol and said PDE5 inhibitor at essentially the same time. The pharmaceutical composition can be designed such that 3-alpha-androstanediol and a PDE5 inhibitor are released (directly) upon administration or such that 3-alpha-androstanediol and a PDE5 inhibitor are released after a certain amount of time has passed (for example 2 hours). This depends on the used formulation of the two ingredients.

The active ingredients (for example 3-alpha-androstanediol and aPDE5 inhibitor) may be present in any suitable form, such as in the form of tablets, capsules, multi-particulates, gels, films, solutions or suspensions and may comprise diluents and/or excipients and/or binders and/or disintegrants and/or lubricants and/or colouring agents. Also different kinds of release patterns can be applied, such as direct release or delayed release.

Because the effects of the different active ingredients must at least partly coincide and preferably completely coincide, the invention preferably also provides instructions as to the administration. Therefore, the invention also provides a kit of parts comprising at least one pharmaceutical composition comprising 3-alpha-androstanediol and at least one composition comprising a PDE5 inhibitor, wherein said kit further comprises instructions in respect to the administration of said compositions.

The invention also provides a kit of parts comprising a pharmaceutical composition as herein described, i.e. a pharmaceutical composition comprising 3-alpha-androstanediol and a PDE5 inhibitor.

In order to further enhance the effects of the kit of parts of the invention said kit may further comprise means for cognitive interventions and stimulation. Such information may be present on any data carrier (paper, CD, DVD), passive or interactive, or it may be a link to a website at least partially designed for the purpose of said cognitive stimulation. Sometimes it is preferred to present said cognitive stimulatory information subconsciously e.g. subliminally.

The herein described combinations of active ingredients may further be accompanied by other suitable active ingredients.

The invention further provides a method for treating a male or a female suffering from sexual dysfunction by providing said male or female with a effective amount of a combination of 3-alpha-androstanediol and a PDE5 inhibitor.

The invention will be explained in more detail in the following, non-limiting examples.

EXPERIMENTAL PART

Experiment 1 3-alpha-androstanediol and sildenafil in FSD

Efficacy of combined administration of 3-alpha-androstanediol and a PDE5 inhibitor-sildenafil- on VPA in response to erotic film excerpts in women with FSD In a double-blind, randomly assigned placebo controlled cross-over design, a group of 16 women with female sexual dysfunction (FSD) will receive 1. 3-alpha-androstanediol (0.1 mg) and sildenafil (10 mg)
2. 3-alpha-androstanediol (0.1 mg) alone
3. placebo on 3 separate experimental days.

The vaginal pulse amplitude will be measured in response to neutral and erotic film excerpts, directly after drug administration, and 1 hour after drug administration. The three experimental days will be separated by (at least) a three-day period. On all drug administrations, subjects will receive one capsule consisting of either sildenafil, or a placebo, and one liquid formulation with either 3-alpha-androstanediol or placebo. Both capsule and liquid formulation will be taken at the same time, one hour prior to testing. The effect of sublingual 3-alpha-androstanediol and will overlap with high sildenafil serum concentrations (Tmax of sildenafil 30-120 min; T1/2=3.5 hours).due to their similar time lag (0-1 hour).

During the experimental session, the subject must insert a tampon-shaped vaginal probe (a photoplethysmograph) in order to measure the VPA. Then subjects will view a 10 minute neutral fragment, followed by a 5 minute erotic film fragment. After these baseline measurements, the subjects receive one of the four medication combinations as described above. Following medication another set of neutral (5 minutes) and erotic (5 minutes) film fragments is shown. The vaginal probe will then be removed. After 4 hours another VPA measurement will be made in response to neutral (5 minutes) and erotic (5 minutes) film fragments. Blood pressure (supine and standing), heart rate, respiration rate, and body temperature will be monitored throughout on the experimental days.

The experiment will be preceded by a screening visit. In this screening visit subjects are interviewed and examined by a resident of the department of gynaecology of Flevo Hospital, Almere to diagnose for FSD and to determine eligibility for study participation. Subjects will be asked to fill out a questionnaire; the Female Sexual Function Index (FSFI). Subjects will be screened to exclude pregnancy or breast feeding, vaginal infections, major operations to the vagina and/or vulva, undetected major gynaecological illnesses or unexplained gynaecological complaints. Weight, height, blood pressure (supine and standing) will be measured. Cardiovascular condition will be tested and ECG checked for significant abnormalities. Subjects with a history of endocrinological, neurological or psychiatric illness and/or treatment. Standard blood chemistry and hematology tests will be performed. Participants are required not to use alcohol or psychoactive drugs the evening before and the day of experimentation. During period of menstruation, subjects will not be tested.

Experiment 2-alpha-androstanediol and sildenafil in MSD

Efficacy of combined administration of 3-alpha-androstanediol and a PDE5 inhibitor-sildenafil- on male sexual function in response to erotic film excerpts in men with MSD In a double-blind, randomly assigned placebo controlled cross-over design, a group of 16 men with male sexual dysfunction (MSD) will receive
1. 3-alpha-androstanediol (0.5 mg) and sildenafil (10 mg)
2. 3-alpha-androstanediol (0.5 mg) alone
3. placebo
on 3 separate experimental days.

The penile tumescence and rigidity will be measured in response to neutral and erotic film audiovisual stimulation (VSTR), directly after drug administration, and 1 hour after drug administration, directly followed by measurement of vibrotactile stimulation ejaculatory latency time (VTS-ELT) and postejaculatory erectile refractory time. The three experimental days will be separated by (at least) a three-day period. On all drug administrations, subjects will receive one capsule consisting of either sildenafil, or a placebo, and one liquid formulation with either 3-alpha-androstanediol or placebo. Both capsule and liquid formulation will be taken at the same time, one hour prior to testing. The effect of sublingual 3-alpha-androstanediol and will overlap with high sildenafil serum concentrations (Tmax of sildenafil 30-120 min; T1/2=3.5 hours).due to their similar time lag (0-1 hour).

The experiment will be preceded by a screening visit. In this screening visit subjects are interviewed and examined by a resident of the department of gynaecology of Flevo Hospital, Almere to diagnose for MSD and to determine eligibility for study participation. Subjects will be asked to fill out a questionnaire; the international index of erectile function questionnaire (IIEF). Weight, height, blood pressure (supine and standing) will be measured. Cardiovascular condition will be tested and ECG checked for significant abnormalities. Participants are required not to use alcohol or psychoactive drugs the evening before and the day of experimentation.

Experiment 3 Animal Model FSD

Efficacy of combined administration of 3-alpha-androstanediol, and a PDE5 inhibitor on female sexual function.

The effect of administration of 3-alpha-androstanediol and sildenafil, on female sexual behaviour in rats, will be investigated. Specifically, proceptive behaviour (soliciting, social interaction time, sniffing) and receptive behaviour (lordosis) of female rats shall be scored for a period of three hours after injection and placement with a single sexually active male rat.

The experiment shall be conducted in a blind, randomly assigned placebo controlled cross-over design, on a group of 32 healthy, sexually active adult female rats. Both female and male rats shall be individually housed for two weeks prior to their (first) day of testing. All drugs and placebo shall be administered by a single intraperitoneal injection. Drug doses are to be established based on literature. Individual rats shall be subjected to no more than two treatments, separated by one week.

Experiment 4 Animal Model MSD

Efficacy of combined administration of 3-alpha-androstanediol and a PDE5 inhibitor on male sexual function The effect of administration of 3-alpha-androstanediol and sildenafil on male sexual behaviour in rats, will be investigated. Specifically, mount latency, mount frequency, intromission latency, intomission frequency, ejaculation latency and post-ejaculatory interval of male rats shall be scored for a period of three hours after injection and placement with a single sexually active female rat.

The experiment shall be conducted in a blind, randomly assigned placebo controlled cross-over design, on a group of 32 healthy, sexually active adult male rats. Both female and male rats shall be individually housed for two weeks prior to their (first) day of testing. All drugs and placebo shall be administered by a single intraperitoneal injection. Drug doses are to be established based on literature. Individual rats shall be subjected to no more than two treatments, separated by one week.

REFERENCES

1. Laumann, E. O., A. Paik, and R. C. Rosen, *Sexual dysfunction in the United States: prevalence and predictors*. Jama, 1999. 281(6): p. 537-44.
2. Reddy, D. S., et al., *A high-performance liquid chromatography-tandem mass spectrometry assay of the androgenic neurosteroid 3alpha-androstanediol (5alpha-androstane-3alpha,17beta-diol) in plasma*. Steroids, 2005. 70(13): p. 879-85.
3. Jin, Y. and T. M. Penning, *Steroid 5alpha-reductases and 3alpha-hydroxysteroid dehydrogenases: key enzymes in androgen metabolism*. Best Pract Res Clin Endocrinol Metab, 2001. 15(1): p. 79-94.
4. Wudy, S. A., et al., *Androgen metabolism assessment by routine gas chromatography/mass spectrometry profiling of plasma steroids: Part 1, Unconjugated steroids*. Steroids, 1992. 57(7): p. 319-24.

The invention claimed is:
1. A method to treat sexual dysfunction which method comprises acute administration on demand to a subject in need of such treatment and who anticipates sexual activity of an effective amount of 3-alpha-androstanediol and an effec- tive amount of a type 5 phosphodiesterase (PDE5) inhibitor, wherein the 3-alpha-androstanediol and the PDE5 inhibitor are released in said subject approximately one hour prior to said sexual activity so that their peak effects at least partly coincide.

2. The method of claim 1, wherein said subject is male.

3. The method of claim 1, wherein said subject is female.

4. The method of claim 1, wherein the PDE5 inhibitor is selected from sildenafil, vardenafil and tadalafil.

5. The method of claim 1, wherein said 3-alpha-androstanediol is administered in a formulation which releases all 3-alpha-androstanediol within one short burst.

* * * * *

UNITED STATES PATENT AND TRADEMARK OFFICE
CERTIFICATE OF CORRECTION

PATENT NO.        : 8,653,051 B2
APPLICATION NO.   : 12/513355
DATED             : February 18, 2014
INVENTOR(S)       : Tuiten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1234 days.

Signed and Sealed this

Twenty-ninth Day of September, 2015

Michelle K. Lee
*Director of the United States Patent and Trademark Office*